United States Patent
Mammone et al.

(10) Patent No.: US 7,291,340 B2
(45) Date of Patent: Nov. 6, 2007

(54) EXTRACTS FROM BLACK YEAST FOR WHITENING SKIN

(75) Inventors: Thomas Mammone, Farmingdale, NY (US); Neelam Muizzuddin, Bethpage, NY (US); Steven F. Schnittger, Huntington Station, NY (US)

(73) Assignee: ELC Management LLC, New York, NY (US)

( * ) Notice: Subject to any disclaimer, the term of this patent is extended or adjusted under 35 U.S.C. 154(b) by 0 days.

(21) Appl. No.: 11/322,014

(22) Filed: Dec. 29, 2005

(65) Prior Publication Data

US 2007/0154444 A1   Jul. 5, 2007

(51) Int. Cl.
*A61K 36/062*   (2006.01)

(52) U.S. Cl. .................................. 424/195.16

(58) Field of Classification Search ...................... None
See application file for complete search history.

(56) References Cited

U.S. PATENT DOCUMENTS

| | | | |
|---|---|---|---|
| 5,578,296 A * | 11/1996 | Kashino et al. ............... | 424/62 |
| 5,627,157 A | 5/1997 | Hijiya et al. | |
| 5,643,587 A | 7/1997 | Scancarella et al. | |
| 5,792,931 A * | 8/1998 | Duvick et al. .............. | 800/301 |
| 6,337,320 B1 | 1/2002 | Hersh et al. | |
| 6,514,506 B1 * | 2/2003 | Mammone et al. ......... | 424/401 |

FOREIGN PATENT DOCUMENTS

| | | |
|---|---|---|
| EP | 0 373 107 A2 * | 6/1990 |
| JP | 07-010734 | 1/1995 |
| JP | 07-274977 | 10/1995 |
| JP | 09-124438 | 5/1997 |

* cited by examiner

*Primary Examiner*—Christopher R. Tate
*Assistant Examiner*—Melenie McCormick
(74) *Attorney, Agent, or Firm*—Cynthia R. Miller (57) ABSTRACT

The present invention relates to topical skin whitening compositions comprising a whitening effective amount of a black yeast-derived melanin-degrading enzyme extract and a method of preparing the compositions. The compositions provide a whitening effect by degrading melanin on the surface of the skin, the hair and the nails. The enzyme extract can be derived from *Exophiala mansonii*. The compositions containing the enzyme extract are more effective than are similar compositions containing kojic acid in producing a whitening effect on the skin.

7 Claims, 5 Drawing Sheets

EXTRACTS FROM BLACK YEAST FOR WHITENING SKIN

FIELD OF THE INVENTION

The invention relates to the field of cosmetics. More specifically, the invention relates to whitening compositions comprising black yeast enzyme extract. The enzyme extract, when topically applied, degrades melanin on the surfaces of the skin, the nails or in the hair. The enzyme extract can be derived from organisms of the many genera of black yeast, such as the genus *Exophiala*, for example, from *Exophiala mansonii*.

The human skin is variously colored, showing individual variations even within racial groups. The appearance of the skin is mainly determined by melanin, a pigment manufactured by melanocytes which are found among the basal cells of the epidermis.

Melanin is a water-insoluble polymer of various compounds derived from the amino acid tyrosine. It is one of two pigments found in human skin and hair and adds brown to skin color; the other pigment is carotene which contributes yellow coloring. The synthesis of melanin reactions is catalyzed by the enzyme tyrosinase. Tyrosinase is found in only one specialized type of cell, the melanocyte, and in this cell melanin is found in membrane-bound bodies called melanosomes. The various hues and degrees of pigmentation found in the skin of human beings are directly related to the number, size, and distribution of melanosomes within the melanocytes and other cells. Besides its role in pigmentation, melanin, which absorbs ultraviolet light, plays a protective role when skin is exposed to the damaging rays of the sun. It is melanin, produced in response to the stimulus of UV light, which is responsible for the tanning of the skin. A suntan functions to protect skin from the harmful effects of UV light.

Although the heterogeneous distribution of melanin in the skin, for example, in the form of freckles or moles, is considered by some as a defining characteristic of beautiful skin, such "beauty marks", on the other hand, often are found to be less desirable by others who seek to lighten these darkened areas of the skin. Even in cases where the skin is homogeneously dark, it is often desired to lighten the skin overall. Whitening agents are typically used for these purposes. Various classes of whitening agents, having different methods of lightening the appearance of the skin, are known.

Tyrosinase inhibitors, such as kojic acid, interfere with the synthesis of melanin in the melanocytes of the skin. Melanin is synthesized by transformation of the precursor tyrosine into the precursor dopa, and into the further precursor dopa-quinone by the enzymatic action of tyrosinase. Then, oxidation to indole-5,6-dihydroquinone occurs, prior to polymerization into melanin. The inhibition of any of the precursors produced via tyrosinase in the synthetic pathway prevents melanin from being formed and can achieve a depigmenting or whitening effect on the skin. Nevertheless, tyrosinase inhibitors will not be effective on already formed melanin.

Other whitening agents include bleaching agents, for example, hydrogen peroxide, hydroquinone, 4-isopropylcatechol and hydroquinone monobenzyl ether. These agents have the disadvantage of requiring repeat application as the top layer of the skin is shed. Bleaching agents have a further disadvantage in that they may be irritating because of their strength. Additionally, such agents may cause vitiligo (leucoderma).

Ascorbic acid, salicylic acid and lactic acid also have also been used as whitening agents. These acids function to cause the top layer of the skin to shed. This method requires repeated applications and long term use to produce a whitening effect.

Yet another method of whitening the skin involves the decomposition of already formed melanin using an enzyme extract of Basidiomycetes or any wood-rotting fungus having melanin-decomposing potency. This method is described in, for example, U.S. Pat. No. 5,578,296. However, the decomposition of melanin on the skin surface does not prevent new darkened spots from being developed in the skin, and therefore requires repeat application as in other whitening methods. This method does not interfere with melanin production and its UV-protecting effect. Additionally, a melanin-degrading enzyme extract derived from *Aspergillus fumigatus* is described in U.S. Pat. No. 6,514, 506.

Cosmetic compositions for lightening skin by a melanin-decomposing action or by a melanin-suppressing function comprising yeast extract or live yeast belonging to the genus *Saccharomyces* have been described. See for example, JP 09-124438, JP 07-274977, JP 07-010734, U.S. Pat. Nos. 5,643,587, and 6,337,320.

It now has been surprisingly discovered that a black yeast-derived enzyme extract in a cosmetic or dermatological composition can be useful as a whitening agent for the skin and the nails and as a lightening agent for hair color.

In accordance with the present invention, a whitening composition is provided which can produce a whitening effect upon application to the skin and the nails and a lightening effect on the hair without the aforementioned disadvantages of other methods, and without the necessity of being combined with other types of whitening treatment.

SUMMARY OF THE INVENTION

The present invention relates to a topical cosmetic or dermatological composition for application to the skin and the nails that comprises a whitening effective amount of an enzyme extract derived from black yeast. The present invention also concerns a topical cosmetic or dermatological composition for application to the hair that comprises a lightening effective amount of an enzyme extract derived from black yeast. The enzyme extract can be obtained from various species of black yeast, including those of the genus *Exophiala*. The melanin-degrading enzyme extract can be derived from *Exophiala mansonii* (*Exophiala castellanii*). The crude enzyme extract preferably is purified before it is added to the cosmetic or dermatological composition.

The present invention also is directed to the method of whitening the skin by topically applying to the skin the compositions containing the black yeast-derived enzyme extract. A method of lightening the color of the hair by topically applying to the hair the compositions containing black yeast-derived enzyme extract is also discussed. Further described is the method of degrading melanin in the skin, and the method of inhibiting a UV-B-induced suntan by topical application of the compositions of the present invention.

DETAILED DESCRIPTION OF THE INVENTION

The Kingdom of Fungi is a significant eukaryotic group equal in importance to animals and plants. While animals require a stomach to digest materials for their nutrients, fungi actually live in or on their food supply, and, as the local environment becomes nutrient depleted, merely grow into new food supplies. In nature, fungi are generally the primary decomposer organisms. Fungi have the important ecological role of breaking down dead material and recycling nutrients through their ecosystem. The fungi can be free-living in decaying woody material, soils, leaf litter, water, dead animals and animal exudates. Others may form symbiotic associations with plants, animals and prokaryotes. Still others are the causative agents of human infections.

Black yeasts are yeast-like fungi which are characterized by their black colonies, the pigment resulting from the production of melanin. The black yeasts include the organisms of the genera *Exophiala, Aureobasidium, Hortae, Wangiella, Phaeoannellomyces,* and the like. Various studies have indicated that the virulence of such dematiaceous fungi is influenced by the presence of melanin. After the melanin biosynthetic pathway gene of *Wangiella dermatitidis* was disrupted, a resulting mutant was shown to be more susceptible to killing by neutrophils and to be less virulent in an acute mouse model. The mutant was shown to regain resistance to neutrophil killing and to exhibit normal virulence in mice when melanin biosynthesis was reconstituted by complementation with the wild type gene, as discussed in "Molecular Cloning and Characterization of WdPKS1, a Gene Involved in Dihydroxynaphthalene Melanin Biosynthesis and Virulence in *Wangiella (Exophiala) dermatitidis*", Infection and Immunity, vol. 69, No. 3, pp. 1781-1794 (March 2001).

It has now been surprisingly discovered that black yeasts, which produce melanin, also possess a melanin-degrading enzymatic activity, and that the topical application to the skin of a cosmetic or dermatological preparation containing an enzyme extract derived from the black yeasts is effective in whitening the skin, and that topical application to the hair of a cosmetic or dermatological preparation containing an enzyme extract derived from the black yeasts is effective in lightening the color of hair.

The black yeast *Exophiala,* of the phylum Ascomycota (sac fungi), is a widespread genus of saprobic fungi, commonly found in decaying wood, in soil enriched with organic wastes, in sewage, and in water.

*Exophiala* are initially yeast-like, moist and brownish to greenish black in color, and subsequently demonstrate a velvety or downy appearance due to the development of short, aerial grayish hyphae. Mature colonies are olive-black on the front and black on the back. This genus lacks morphological evidence of a sexual state. As the cultures mature, septate hyphae which bear conidia are eventually formed. The fungi are spread by the release of the conidia from the hyphae.

The genus *Exophiala* contains many species. The most common include *E. jeanselmei, E. dermatitiidis, E spinifera, E. catellanii (mansonii), E. bergeri, E. moniliae, E. phaeomuriformis, E. pisciphila,* and *E. salmonis*.

The melanin-degrading enzyme extract of the present invention can be prepared by growing colonies of *E. mansonii* in Malt agar medium at 26° C., propagated and commercially available from American Type Culture Collection (ATCC), Manassas, Va. A preferred strain is designated CBS 158.58, and is available in freeze-dried form. *E. mansonii*, obtained from ATCC, is grown in a fermentation process at 26° C., preferably in Malt enzyme extract broth, in a one-liter spinner flask, and is grown to a density in the range of about $10^6$ to $10^7$ colony forming units per ml (cfu/ml).

The enzyme extract is collected by centrifuging a 500 ml batch of the culture and resuspending it in about 150 mM NaCl, about 50 mM Tris buffer, and about 1 percent NP40 detergent, and then sonicating the resuspension for about 30 minutes. The enzyme extract then may be added, in crude form, directly to a cosmetic or dermatological formulation. Preferably, however, the enzyme extract is purified by filtering it through a 0.22 μm filter. The amount of enzyme in the purified enzyme extract solution can be from about 1 to about 95 percent, preferably from about 80 to 95 percent, of the purified solution.

The enzyme extract is incorporated into a cosmetic or dermatological formulation in a whitening effective amount. The term "whitening effective amount" as used herein means that amount of enzyme extract which reduces (lightens) the color of the skin or the nails or the hair, as measured using a Minolta Chromameter, by about at least about 20 percent, preferably by at least about 30 percent. The whitening effective amount can be in the range of from about 0.01 to about 99.9 percent enzyme extract by weight of the total composition. Preferably, the whitening effective amount is in the range of from about 0.05 to about 20 percent enzyme extract by weight of the total composition. More preferably, the whitening effective amount is in the range of from about 0.05 to about 5.0 percent enzyme extract by weight of the total composition. Most preferably, the whitening effective amount is in the range of from about 0.1 to 2 percent enzyme extract by weight of the total composition.

The present invention also includes the method of whitening the skin and the nails and lightening the color of the hair by incorporating in the cosmetic or dermatological formulation the whitening (lightening) effective amount of the enzyme extract, and applying the composition to the skin, the nails or the hair. The whitening compositions are applied to the skin and nails by rubbing on about 2 mg/cm$^2$ of skin surface, and reapplied as necessary, for example, on a daily basis. The compositions of the present invention may be prepared in any form convenient for topical application to the skin, the nails, or the hair, including, but not limited to, gels, creams, colloidal dispersions, emulsions (water-in-oil or oil-in-water), suspensions, solutions, lotions, foams, mousses, sprays and the like. Preferably, the composition is applied to the skin in a cream form, and to the nails in a cream or a spray form. A leave-in lotion or a spray is the preferred form of the composition of the invention for application to the hair.

The compositions of the present invention are formulated with any cosmetically or dermatologically acceptable vehicle or carrier; that is, a carrier which will deliver the whitening or lightening effective amount of the enzyme extract and any other actives which may be present in the composition safely to the target area without adverse effect on the enzyme extract and other actives. Suitable carriers include, but are not limited to, water, acetone, ethanol, ethylene glycol, propylene glycol, butane-1,3-diol, isopropyl myristate, isopropyl palmitate and mineral oil.

The compositions of the present invention may be combined with one or more sunscreens, including, but not limited to, titanium dioxide, zinc oxide, benzophenones, p-amino benzoic acid (PABA), octyl dimethyl PABA, amyldimethyl PABA, octyl methoxycinnamate, 2-ethoxy p-methoxycinnamate, oxybenzone, homosalate, phenyl salicylates, glyceryl p-amino benzoate, ethyl-p-glycosylimido benzoate and the like. The sunscreens are used in amounts typically used for those agents.

Various other optional ingredients may be included with the compositions of the present invention, including but not limited to, fragrances, perfumes, flavorings, preservatives, emollients, antiseptics, pigments, dyes, colorants, humectants, propellants, waterproofing agents, film formers, vitamins as well as other classes of materials whose presence may be cosmetically, dermatologically, pharmaceutically, or otherwise desirable. Common examples may be found in the CTFA International Cosmetic Ingredient Dictionary 12th Edition, The Cosmetic, Toiletry, and Fragrance Association, Inc., Washington, D.C., 2004, the contents of which are incorporated herein. The whitening compositions may also be used in makeup products.

The compositions of the present invention may also comprise additional useful active ingredients which include, but are not limited to, other known whitening agents, such as for example, tyrosinase inhibitors such as, for example, kojic acid and its derivatives, hydroquinones and their derivatives, one such hydroquinone derivative being arbutin, licorice enzyme extract and its derivatives, ascorbic acid and its derivatives, and azelaic acid; antioxidants; antimicrobials; analgesics; anesthetics; anti-acne agents; antidermatitis agents; antipruritic agents; antiinflammatory agents; antihyperkeratolytic agents; anti-dry skin agents; antiperspirants; antipsoriatic agents; antiseborrheic agents; antiaging agents; antiwrinkle agents; self-tanning agents; wound-healing agents; corticosteroids; and hormones. The incorporation of the active in the formulation is determined by its solubility and/or stability in combination with the black yeast-derived melanin-degrading enzyme extract of the present invention. The selection of the mode of delivery for additional active ingredients, however, is limited to the mode of delivery chosen for the whitening compositions.

The invention is further illustrated by the following non-limiting examples.

EXAMPLES

Example 1

Efficacy of *Exophiala mansonii* Extract in Degrading Melanin

Figure 1:
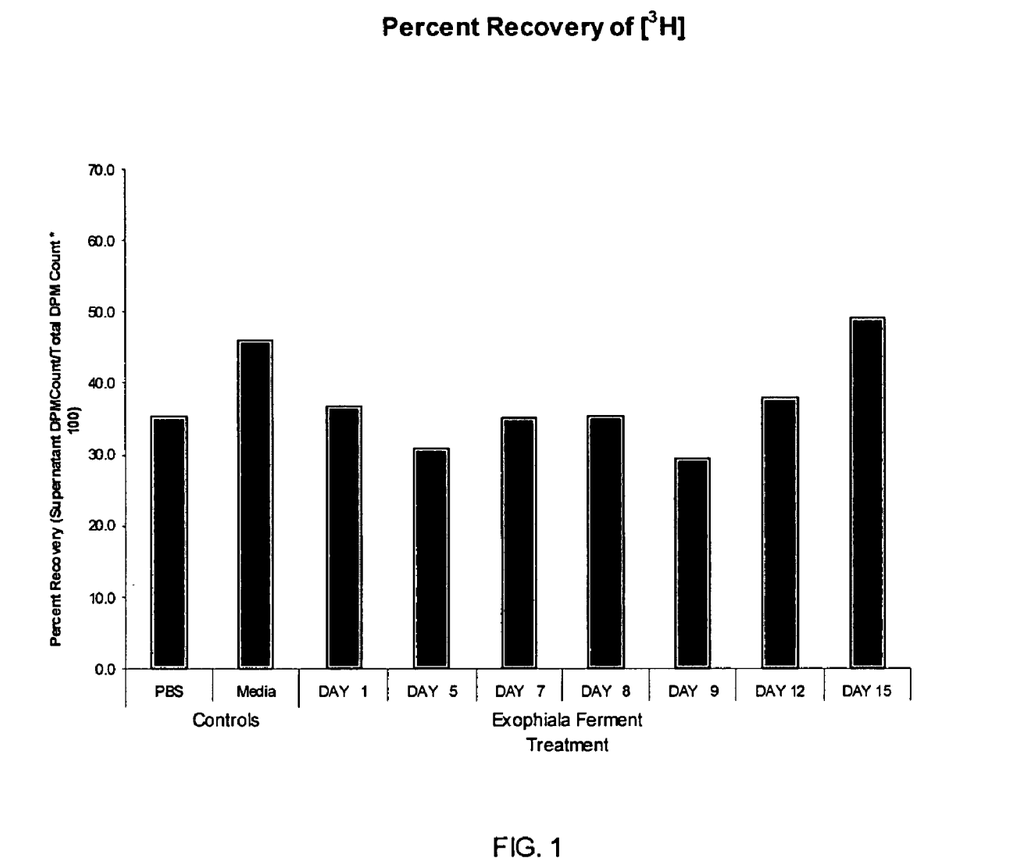
FIG. 1 is a chart demonstrating the ability of *Exophiala mansonii* ferments to degrade synthetic melanin as measured by the percent recovery of [$^3$H] at day 1, 5, 7, 8, 9, 12 and 15.

The efficacy of *Exophiala mansonii* extract in degrading melanin is demonstrated by growing the yeast in a fermentation process, and introducing 1, 5, 7, 8, 9, 12 and 15 day 0.22 μm filtered ferment to individual microcentrifuge tubes containing 100 μl aliquots of [$^3$H]-synthetic melanin. PBS and growth medium serve as controls. The tubes are pulse-vortexed and placed in a 37° C. oscillating incubator. The tubes are incubated for three days, and once each day the tubes are pulse vortexed to facilitate melanin degradation. The tubes are removed from the incubator after three days, pulse vortexed, and centrifuges at maximum g for 10 minutes. The supernatant in each tube is carefully separated from the pelleted material, and introduced into a scintillation vial. The pellet in each tube is resuspended in 200 μl of PBS and transferred to a separate scintillation vial. To each vial, 5 ml of scintillation cocktail is added. Disintegrations of [$^3$H] are determined using a LKB Wallac scintillation counter using program A12. The efficacy of the ferments in degrading melanin is determined by the following formula:

$$\text{Efficacy} = 100\% \times \frac{[^3H] \text{ in the supernatant}}{\text{total } [^3H] \text{ in microcentrifuge tube}}$$

As shown in FIG. 1, the percent recovery of [$^3$H] increases linearly starting at day 9, with peak recovery at day 15. The degradation of synthetic melanin by 15 day ferment results in a 49.2% recovery of [$^3$H].

Example 2

Efficacy of *Exophiala mansonii* Extract in Degrading Melanin

Figure 2:
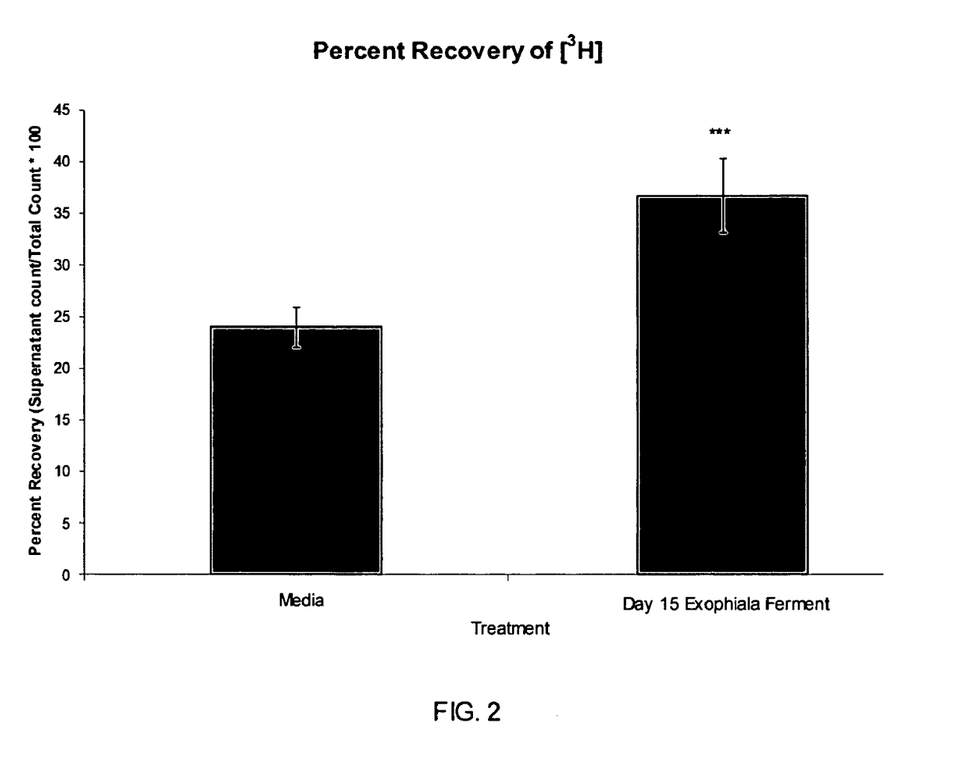
FIG. 2 is a chart demonstrating the ability of day 15 *Exophiala mansonii* ferment to degrade synthetic melanin as measured by the percent recovery of [$^3$H] at day 15.

The efficacy of 15 day filtered ferment of *Exophiala mansonii* in degrading melanin is analyzed as demonstrated in Example 1. Growth medium served as a control. The results are shown in FIG. 2. The degradation of synthetic melanin by 15 day *Exophiala* ferment results in a 37% recovery of [$^3$H]. ** represents p=<0.01. Error bars represent SD, n=3.

Example 3

Efficacy of *Exophiala mansonii* Extract in Degrading Melanin

Figure 3:
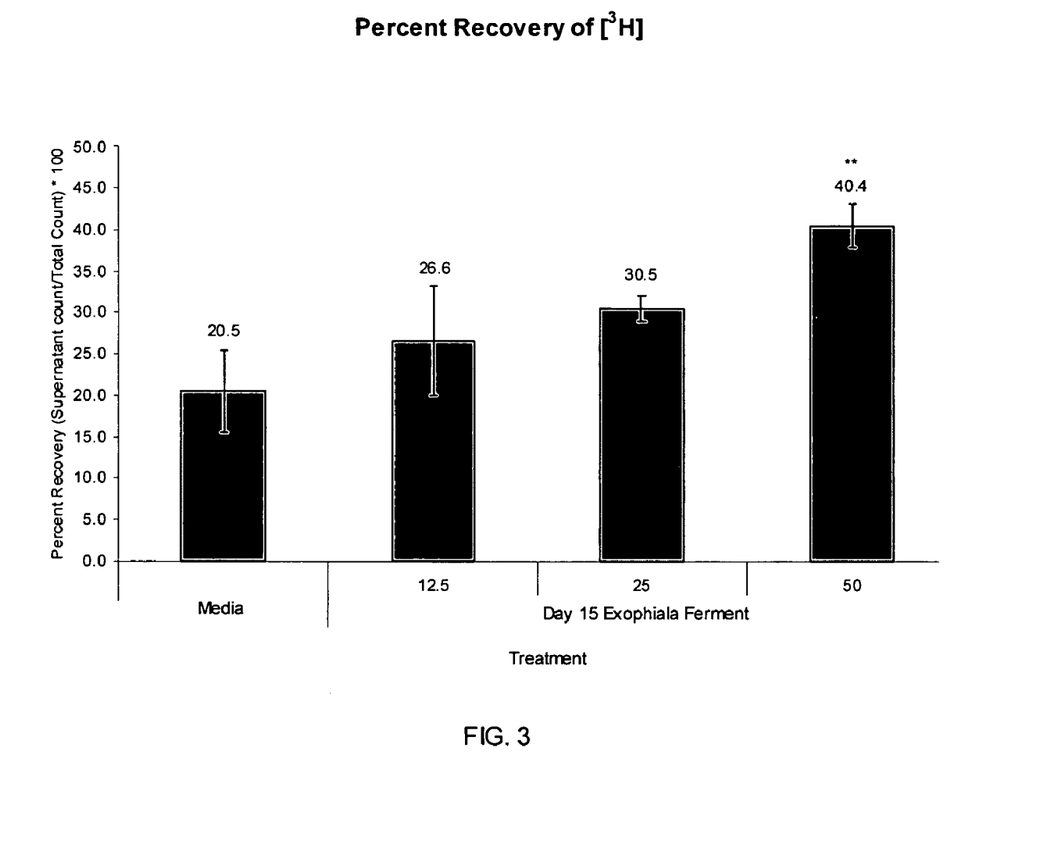
FIG. 3 is a chart demonstrating the degradation of synthetic melanin by day 15 *Exophiala mansonii* ferment in a dose dependent manner as measured by the percent recovery of [$^3$H].

The efficacy of Exophiala mansonii extract in degrading melanin is demonstrated as in Example 2, except that the 15 day filtered ferment is assayed at final concentrations of 50%, 25% and 12.5%. The 25% and 12.5% samples are diluted with growth medium. It is observed from FIG. 3 that the 15 day ferment degrades synthetic melanin in a dose dependent manner. The percent recovery of [3H] is 26.6%, 30.5% and 40.4% at final concentrations of 12.5%, 25% and 50% of *Exophiala mansonii* extract, respectively. *** represents p=<0.001. Error bars represent SD, n=3.

Example 4

Preparation of a Whitening Composition

| Material | Weight Percent |
|---|---|
| Phase I | |
| Water/phenyl trimethicone/cyclomethicone/dimethiconol/ phosphoglycerides/carbomer/triethanolamine | 50.00 |

-continued

| Material | Weight Percent |
| --- | --- |
| Sodium Dehydroacetate | 0.10 |
| Disodium EDTA | 0.14 |
| Phase II | |
| Glycerin | 3.00 |
| Aluminum starch octenyl succinate | 1.00 |
| Phase III | |
| Purified water | 40.81 |
| Acrylates/C10–30 alkyl acrylate crosspolymer | 0.30 |
| Carbomer | 0.35 |
| Phase IV | |
| Glycerin | 1.00 |
| Xanthan gum | 0.20 |
| Phase V | |
| Purified water | 2.00 |
| Triethanolamine | 0.10 |
| *Exophiala mansonii* - derived enzyme extract | 1.00 |
| Total | 100.00 |

At room temperature and atmospheric pressure, phase I ingredients, phase II ingredients, phase III ingredients, phase IV ingredients and phase V ingredients are combined in separate vessels. The ingredients of phases II, IV and V are hand mixed in their separate vessels. Phase III ingredients are mixed using a propeller mixer. Phase I ingredients are placed in a homogenizing mixer and stirred. The combined ingredients of phase II are added with stirring to the combined ingredients of phase I, and stirred until uniform. The combined ingredients of phase III are then combined with the uniform mixture of phase I and II ingredients and the mixture stirred until uniform. The combined ingredients of phase IV and then of phase V are separately added to the uniform mixture of phase I, II and III ingredients and mixed until uniform, to form a final soft cream.

Example 5

Whitening Action of *Exophiala mansonii* Enzyme Extract

A comparative study is done to determine the whitening efficacy of an *Exophiala mansonii*—derived enzyme extract in comparison to the efficacy of a known tyrosinase inhibitor, kojic acid. More specifically, the study was designed to study the lightening effect of these materials (reduction in tanning) using the fading of UV-B induced tan as a marker. Two samples are prepared. The first sample contains the composition described in Example 4. The second sample has the same composition as that described in Example 4 except that 2% kojic acid is substituted for the 1 % *Exophiala mansonii* enzyme extract.

Nine volunteers participate in the study. The volunteer panelists are in normal health with no evidence of acute or chronic disease including dermatological problems. The panelists are female, ranging in age from 18-45, and have skin type I-II. The panelists do not exhibit sunburn effects, rashes, scratches or burn marks, which conditions might interfere with the analysis of the test results. Pregnant or lactating volunteers are excluded from the study. Additionally, the skin test site on each panelist is examined for the presence of excessive warts, nevi, moles, sunburn, suntan, scars or active dermal lesions, which also might interfere with the analysis of the test results. Panelists accepted for the study are not using systemic or topical retinoids, antihistamines or similar agents during the course of the study and two weeks prior to commencement of the study.

Distinct areas, corresponding to the test materials, and an additional untreated, irradiated control area, are marked on the backs of each of the panelists. Each area is approximately 4 cm$^2$. Each panelist receives twice the MED of UV-B on each site. The sites are irradiated with a Xenon Arc Solar Simulator (150 Watt) with filters (mm UG-5) to expose the skin to UV-B and UV-A irradiation. Tanning is observed for six days after irradiation at which point color measurements are made using a Minolta Chromameter which measures the difference in reflectance of the skin, L. The change in the value of the difference in reflectance, $\Delta L^*$, is measured against a baseline skin color value of untreated irradiated skin measured on day 6. The test materials are applied on their respective sites at the rate of 2 mg/cm$^2$, and allowed to dry for 10 minutes. Product treatments are continued once a day for 15 days (i.e. day 6 to day 20 of the test). Chromameter readings are obtained on day 6, 8, 11, 13 and 15.

Figure 4:
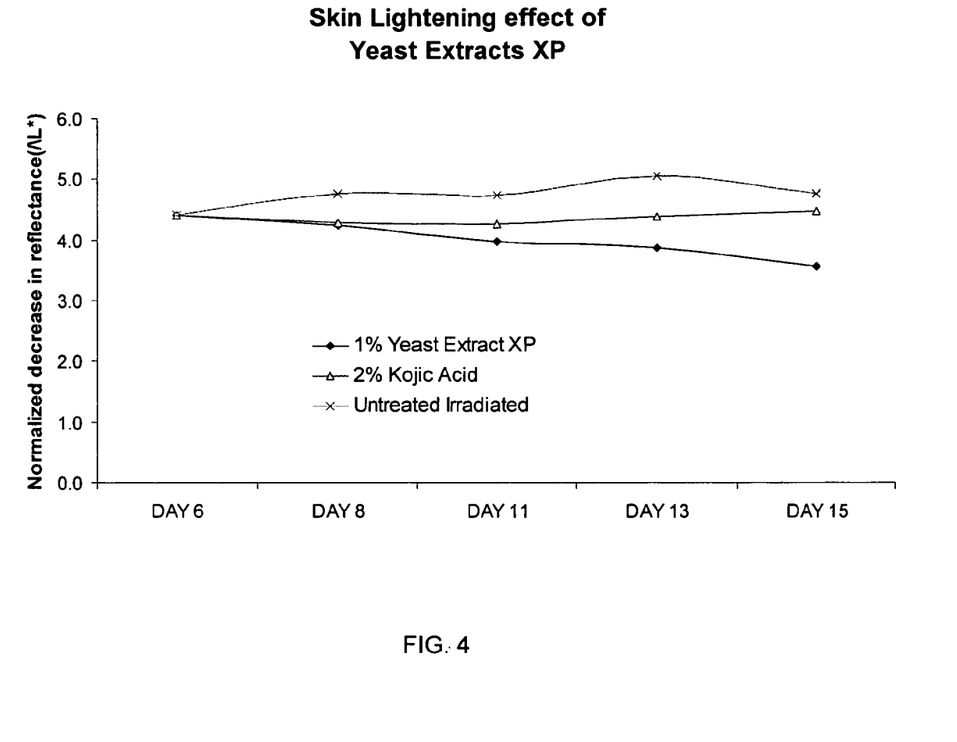
FIG. 4 is a graph illustrating the skin whitening effect on a UV-B induced tan by a 2% kojic acid-containing composition and a the composition of the invention containing 1% *Exophiala mansonii* enzyme extract as measured at day 6, 8, 11, 13 and 15 of a treatment regime as indicated by the change in reflectance values.
Figure 5:
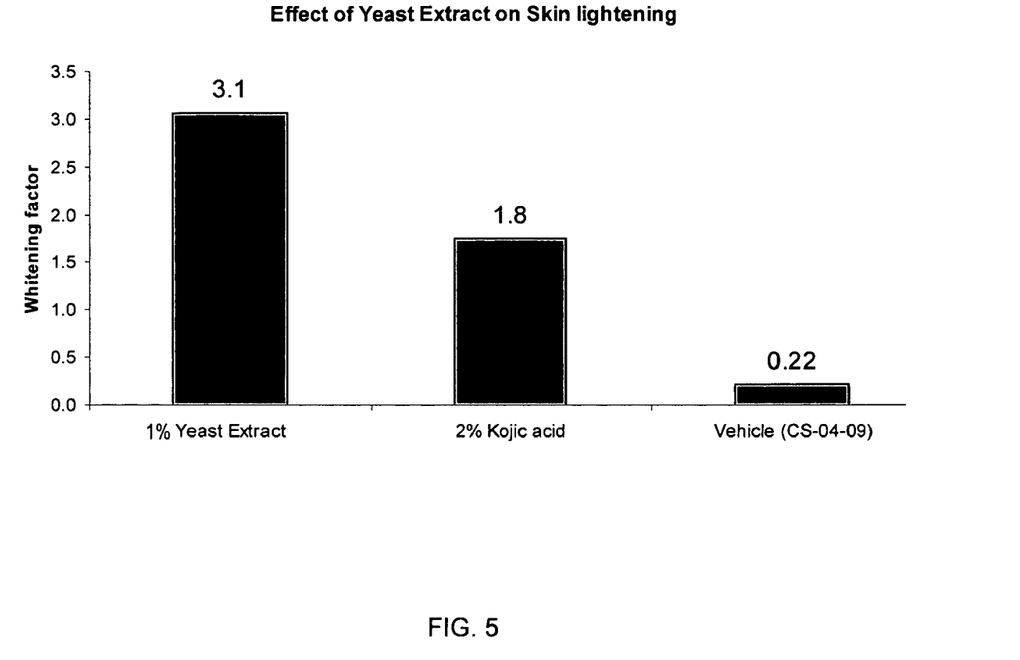
FIG. 5 is a chart of the skin whitening effect of a composition containing 2% kojic acid compared with the skin whitening effect of a composition of the invention containing 1% *Exophiala mansonii* enzyme extract.

Results are shown in FIGS. 4 and 5. FIG. 4 demonstrates that the whitening effect of 1% *Exophiala mansonii* enzyme extract is greater than that of the 2% kojic acid control. The comparison is measured in terms of the change in the value in the difference of reflectance of the skin ($\Delta L^*$) on each of days 6, 8, 11, 13 and 15, compared with the baseline value of the untreated irradiated skin measured on day 6, and it indicates that the enzyme extract-containing compositions of the present invention have a lower change in reflectance and, therefore, a greater whitening effect, i.e. a more rapid fading of an induced tan, as compared with compositions containing twice the amount of kojic acid.

The observed reflectance values for all the time points are recorded, and the area under the curve for each test site was calculated. The Whitening Factor is calculated as the area under the curve of the treated site subtracted from the untreated site, and is shown in FIG. 5. As observed in FIG. 5, the composition containing the *Exophiala mansonii* enzyme extract exhibited an excellent whitening effect, having a whitening factor of 3.1, compared to a composition containing twice the amount of kojic acid, which demonstrated a whitening factor of 1.8.

What we claim is:

1. A method of whitening the skin or the nails, comprising topically applying a composition comprising a black yeast-derived melanin-degrading enzyme extract to the skin or nail, wherein the melanin-degrading enzyme extract is an *Exophiala*-derived enzyme extract.

2. The method of claim 1, wherein the *Exophiala*-derived enzyme extract is obtained from *Exophiala mansonii*.

3. The method of claim 1, wherein the enzyme extract is present in the composition in an amount in the range of from about 0.05 percent to about 20 percent by weight of the total composition.

4. The method of claim 3, wherein the enzyme extract is present in the composition in an amount in the range of from about 0.05 percent to about 5 percent by weight of the total composition.

5. The method of claim 4, wherein the enzyme extract is present in the composition in an amount in the range of from about 0.1 percent to about 2 percent by weight of the total composition.

6. A topical cosmetic or dermatological composition for application to the hair, comprising a black yeast derived melanin-degrading enzyme extract and a cosmetically or dermatologically acceptable carrier, wherein the melanin-degrading enzyme extract is an *Exophiala mansonii*-derived enzyme extract, and wherein the enzyme extract is present in an amount in the range of from about 0.05 to 20 weight percent of the total composition.

7. The composition of claim 6, in which the enzyme extract is present in an amount sufficient to lighten the hair color.

* * * * *